United States Patent [19]

Niziolek et al.

[11] Patent Number: 4,890,920

[45] Date of Patent: Jan. 2, 1990

[54] IN SITU PARTICLE SIZE MEASURING DEVICE

[75] Inventors: James M. Niziolek, Enfield; James P. Sutton, III, Middletown, both of Conn.

[73] Assignee: Combustion Engineering, Inc., Windsor, Conn.

[21] Appl. No.: 41,495

[22] Filed: Apr. 23, 1987

Related U.S. Application Data

[63] Continuation of Ser. No. 828,480, Feb. 12, 1986.

[51] Int. Cl.[4] .............................................. G01N 15/02
[52] U.S. Cl. .................................................. 356/336
[58] Field of Search ..................... 73/866.5, 431, 865.5; 356/336, 338, 343, 340, 438, 439, 441, 442, 446

[56] References Cited

U.S. PATENT DOCUMENTS

| 3,142,180 | 7/1964 | Glezen et al. | 73/865.5 |
|---|---|---|---|
| 3,763,428 | 10/1973 | Preist | 73/865.5 |
| 3,802,271 | 4/1974 | Bertelson | 73/865.5 |
| 3,920,334 | 11/1975 | Steichen et al. | 356/343 |
| 3,954,342 | 5/1976 | Boeke | 356/438 |
| 4,095,775 | 6/1978 | Hotham | 356/336 |
| 4,152,070 | 5/1979 | Kushner et al. | 356/343 |
| 4,167,335 | 9/1979 | Williams | 356/336 |
| 4,188,121 | 2/1980 | Hirleman, Jr. et al. | 356/336 |
| 4,492,467 | 1/1985 | Drain et al. | 356/336 |
| 4,541,719 | 9/1985 | Wyatt | 356/343 |
| 4,595,291 | 6/1986 | Tatsuno | 356/336 |
| 4,647,780 | 3/1987 | Dunkel | 356/438 |

FOREIGN PATENT DOCUMENTS

| 0066342 | 4/1982 | Japan | 356/336 |
|---|---|---|---|
| 0206872 | 12/1983 | Japan | 73/119 |
| 8304098 | 11/1983 | World Int. Prop. O. | 356/343 |

OTHER PUBLICATIONS

Particle and Droplet Sizer, Powder Metallurgy Intl., vol. 10, No. 2, May 1978, p. 99.
Landa, The Measurement and Display of Bubble Size Distribution Using Scattered Light, IEEE Transactions on Instrumentation and Measurement, vol. IM-21, No. 1, Feb. 1972, pp. 57–59.

*Primary Examiner*—Robert R. Raevis
*Attorney, Agent, or Firm*—Arthur E. Fournier, Jr.

[57] ABSTRACT

A particle size measuring device for effecting with regard to particles present in a fluid substance the simultaneous measurement in situ of two parameters thereof; namely, particle size distribution and volumetric density. The particle size measuring device comprises a laser light source (14), a laser light conveying device (40), a collimator, a first focusing device (64), a defined sample path (74) through which particles to be measured pass, a second focusing device (78) and a detector device (82). The mode of operation of the particle size measuring device is such that the laser light from the laser light source (14) is conveyed by means of the laser light conveying device (40) to the collimator. After being collimated the laser light is transmitted to the first focusing device (64) whereby the laser light is focused and is then made to pass across the sample path (74). In the course of passing across the sample path (74), the laser light is scattered by the particles that are present in the sample path (74). Both scattered and collimated light is collected by the second focusing device (78) and the focused thereby on to the detector device (82) such that the intensity distribution of the laser light is gathered by the detector device (82). Particle size distribution is inferred from the light distribution received by the detector device (82) and volumetric density is calculated by means of a predetermined equation.

2 Claims, 4 Drawing Sheets

IN SITU PARTICLE SIZE MEASURING DEVICE

This is a continuation of U.S. patent application Ser. No. 828,480, filed Feb. 12, 1986.

CROSS-REFERENCE TO RELATED APPLICATIONS

This Application is hereby cross-referenced to the following two patent applications which were commonly filed herewith and which are commonly assigned: U.S. patent application, Ser. No. 828,490, filed Feb. 12, 1986, entitled "Pulverized Solid Control System", filed in the names of George F. Shulof and Michael J. DiMonte; and U.S. patent application, Ser. No. 828,479 filed Feb. 12, 1986 entitled "Mounting And Traversing Assembly For In Situ Particle Size Measuring Device", filed in the names of Mark P. Eramo and John M. Holmes, which issued as U.S. Pat. No. 4,665,760 on May 19, 1987.

BACKGROUND OF THE INVENTION

This invention relates to measuring devices, and more specifically to a measuring device that is particularly suited for employment for purposes of effecting measurements simultaneously and in situ of the particle size distribution and volumetric density of particles that are present in a fluid substance.

One of the important parameters in many industrial processes is particle size. As such, it has long been known in the prior art to provide devices that are capable of being employed for purposes of effecting measurements of particles. To this end, the prior art is replete with examples of various types of devices that have been used to obtain measurements of particles. In this regard, in many instances discernible differences exist in the technique by which the measurement of the particles is accomplished. The existence of such differences is, in turn, attributable for the most part to the diverse functional requirements that are associated with the specific application in which such devices are designed to be employed. For instance, in the selection of the particular type of device that is to be utilized for a specific application one of the principal factors to which consideration must be given is that of the nature of the substance of which the particle that is to be measured is formed. Another factor to which consideration must be given is that of the nature of the substance in which the particles are present at the time they are being measured. Yet another factor to which consideration must be given is the relative size of the particles that are to be measured.

Some of the techniques that have been utilized heretodate by the prior art for purposes of accomplishing the measurement of particles include acoustical techniques, optical counting techniques, electrical counting techniques, sedimentation techniques, separation techniques and surface measurement techniques. Moreover, the kinds of particles with which such techniques have been sought to be applied for purposes of making measurements of the particles include such particles as blood particles, food particles, chemical particles, mineral particles as well as others. In addition, diverse ones of the techniques to which reference has been had hereinbefore have been sought to be employed for purposes of accomplishing the measurement of particles while the latter are present in a variety of different types of fluid substances such as various types of gases and various types of liquids.

Unfortunately, however, the devices that have been available in the prior art heretofore for purposes of enabling the techniques to be carried out which have been referred to above have been found to be disadvantageously characterized in one or more respects. To this end, where such devices have been sought to be employed in connection with applications involving industrial processes for purposes of generating information relating to particle size that could be utilized to accomplish, as needed, adjustments to the industrial process, it has not been possible through the use of prior art forms of devices to generate the information required in a sufficiently timely fashion and/or with the desired degree of accuracy. Namely, it has proven to take far too long and/or to require far too much effort to generate the desired information pertaining to particle size for this information to be of any significant value insofar as concerns the utilization thereof for purposes of making timely adjustments to the industrial process. In large measure this is based on the fact that with the prior art devices that have heretofore been available for use for purposes of effectuating particle size measurements it has not been possible to make measurements in situ therewith. As a result, in order to make use of the prior art devices that have been available heretofore there has most often existed a need to collect a sample from the medium in which are present the particles that it is desired to measure, a need to transport this sample to the device that is to be used to accomplish the particle size measurements, a need to actually perform the particle size measurements with the device, and then finally based on the results of the particle size measurements effectuate whatever adjustments must be made to the industrial process in order to ensure that the particles do in fact embody the size that they must have if the particular industrial process from which the particles that were measured were taken is to be successfully operated.

By way of exemplification and not limitation, one form of industrial process in which particle size is known to be an important consideration for the successful operation of the process is the combustion of pulverized coal. As regards the combustion of pulverized coal, it has long been known that an essential component of any steam generation system that utilizes pulverized coal as a fuel is the apparatus in which the coal is pulverized in order to render the coal suitable for such usage. One form of apparatus in particular that has frequently been used for purposes of accomplishing the pulverization of coal, although various types of apparatus have been known to have been employed for this purpose, is that which those in the industry commonly refer to as a bowl mill. The bowl mill obtains its name principally from the fact that the pulverization, i.e., grinding, of the coal that takes place therewithin occurs on a grinding surface which in configuration bears a resemblance somewhat to that of a bowl. By way of illustration, reference may be had to U.S. Pat. No. 3,465,971, which issued Sept. 9, 1969 to J. F. Dalenberg et al and which is assigned to the same assignee as the present invention, for a showing of a prior art form of bowl mill. This patent contains a teaching of both the nature of the construction and the mode of operation of a bowl mill that is suitable for use for purposes of effectuating the pulverization of the coal that is used to fuel a coal-fired steam generator.

The efficient combustion of pulverized coal, particularly as it relates to the use of pulverized coal as a fuel in a steam generation system, requires that the coal particle size be held close to a specified particle size distribution. Typically, for a medium reactivity coal this is 70% passing through 200 mesh, and 1% not passing through 50 mesh. Based on an economic evaluation for a typical 500 MW coal-fired steam generator power plant, it has been determined that through an increase in carbon conversion rate which in turn is achievable by maintaining a specified particle size distribution, it is possible to realize significant savings amounting to hundreds of thousands of dollars on an annualized basis in the cost of operating a power plant of the size to which reference has been made hereinbefore. Obviously, however, the savings that will be actually realized insofar as any specific power plant that is fueled with pulverized coal is concerned by virtue of maintaining the coal particle size close to a specified particle size distribution will be dependent on a number of factors including the reaction kinetics of the coal, i.e., how sensitive the combustion efficiency is to particle size for the specific coal being used, and how well and often control is exercised over the bowl mill to maintain the optimum size distribution of the coal particles. In every instance, however, maintaining the size distribution of the coal particles close to the optimum should result in some measure of fuel savings.

Other benefits should also flow from the fact that better control is being exercised over the size distribution of the coal particles. In this regard, reference is had to the fact that there should be reduced slagging in the steam generator due to better control over the size distribution of the coal particles. In addition, it may be possible in some instances to make use of the fact that deviations are occurring in the size distribution of the coal particles from that which should be present as a maintenance and diagnostic aid to detect problems associated with the operation of the bowl mill in which the pulverization of the particles of coal that have been measured was effected. Also, the possibility exists for exercising continuous control over the operation of the bowl mill through the use of the information garnered from having made coal particle size measurements. Yet another possibility is to utilize the information acquired from the performance of coal particle size distribution measurements for purposes of obtaining an indication of the fuel-to-air ratio in the coal feed pipe by means of which, as is well-known to all, the pulverized coal particles are conveyed from the bowl mill to the steam generator wherein the combustion of the pulverized coal particles takes place.

Thus, there has been evidenced in the prior art a need for a new and improved form of particle size measuring device which would embody a mode of operation whereby it would be possible therewith to rapidly obtain an accurate particle size measurement. Namely, a need has been evidenced for a new and improved form of particle size analyzer that would render it possible to provide an on-line measurement of particle size such that the information derived from such measurements is obtained in a timely fashion whereby this information can be utilized for purposes of effectuating control over an industrial process wherein particle size is an important parameter. That is, a new and improved form of particle size analyzer has been sought whereby it would be possible to make measurements therewith in situ of particle size distribution such that adjustments can be had to an industrial process, when such adjustments are deemed to be necessary based on measurements of particle size distribution. In addition, there has been sought such a particle size analyzer which is further characterized in that simultaneous with the making of the particle size distribution measurement, it is also possible therewith to concurrently obtain measurements in situ of volumetric density.

It is, therefore, an object of the present invention to provide a new and improved measuring device that is operative for purposes of obtaining measurements of the size of particles that are present in a fluid substance.

It is another object of the present invention to provide such a new and improved particle size measuring device which renders it possible through the use thereof to rapidly obtain accurate measurements of particle size.

It is still another object of the present invention to provide such a new and improved particle size measuring device through the use of which it is possible to make in situ measurements of the size of particles that are present in a fluid substance.

A further object of the present invention is to provide such a new and improved particle size measuring device that is operative to effect the measurement in situ of the particle size distribution of particles which are present in a fluid substance.

A still further object of the present invention is to provide such a new and improved particle size measuring device that is operative to effect the measurement in situ of the volumetric density of particles that are present in a fluid substance concurrent with the making of measurements in situ of the particle size distribution of the particles which are present in the fluid substance.

Yet another object of the present invention is to provide such a new and improved particle size measuring device which renders it possible through the use thereof to generate information relating to particle size in a sufficiently timely fashion whereby control may be exercised over an industrial process based on the information derived from the particle size measurements.

Yet still another object of the present invention is to provide such a new and improved particle size measuring device which is relatively simple to manufacture and operate, while yet being relatively inexpensive to provide.

SUMMARY OF THE INVENTION

In accordance with the present invention there is provided a measuring device that is particularly suited for purposes of making measurements of the size of particles. To this end, the subject measuring device is operative for purposes of effecting measurements simultaneously and in situ of the particle size distribution and volumetric density of particles that are present in a fluid substance. In accord with the nature of the construction thereof, the subject particle size measuring device consists essentially of two principal components; namely, a light source portion and a probe head portion. The light source portion preferably is in the form of a helium neon laser. From the laser, light is conveyed by a fiberoptic cable to the probe head whereupon the light exits from the cable, and is spatially filtered and collimated. After being collimated the light is caused to be transmitted to a first focusing lens. The first focusing lens is operative to focus the collimated light across a sample path and on to a second focusing lens that is located on the opposite side of the sample path from that on which the first focusing lens is located. In the course of passing across the sample path, the laser light is scattered by the particles that are present in the sample path. The scattered light in turn is designed to be collected by the second focusing lens, and to be then focused thereby onto a detector device such that the intensity distribution of the light is gathered by the detector device. From the light distribution received by the detector device it is possible to infer particle size distribution, whereas volumetric density is calculated through the use of a particular equation.

DESCRIPTION OF A PREFERRED EMBODIMENT

Figure 1:
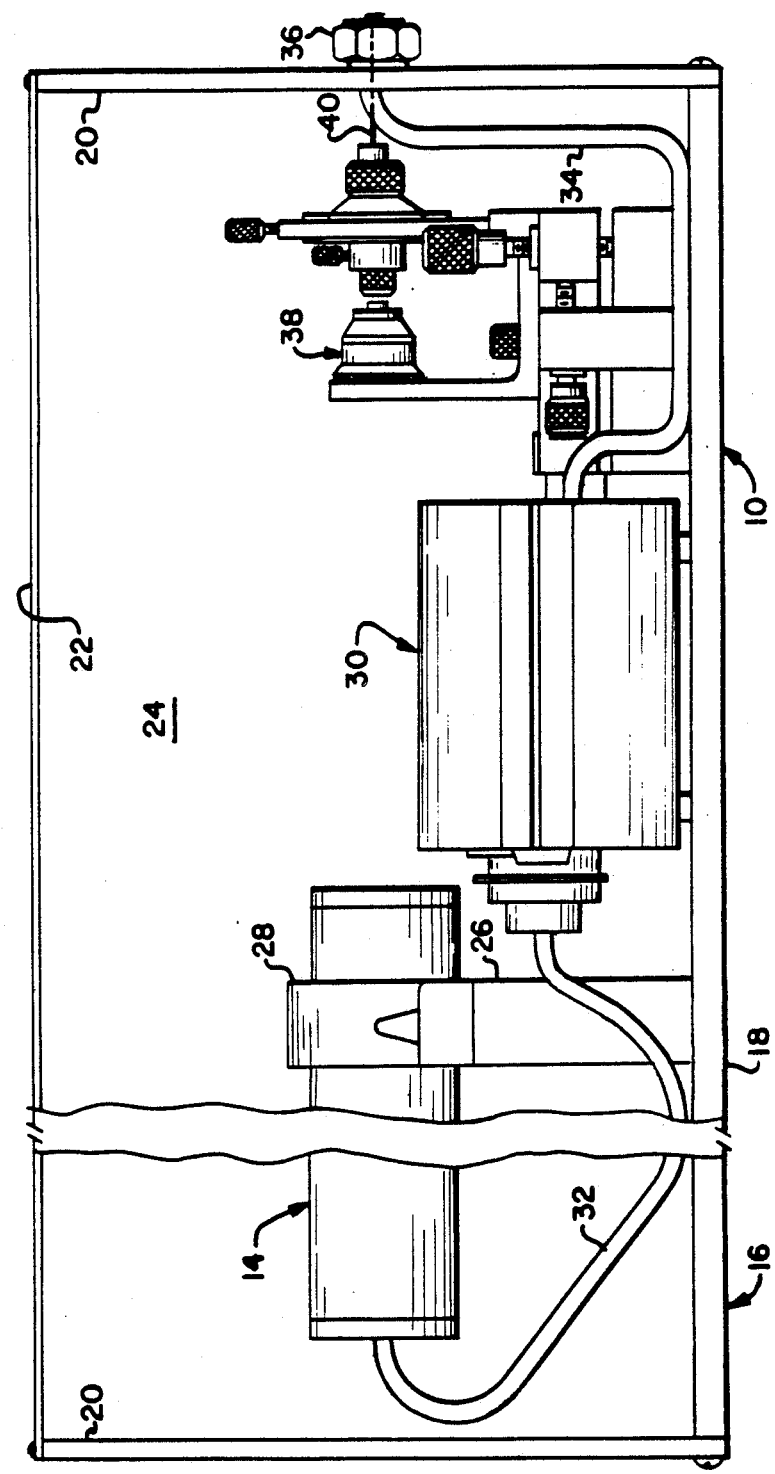
FIG. 1 is a side elevational view of one embodiment of the light source portion that can be employed in a particle size measuring device constructed in accordance with the present invention.
Figure 1A:
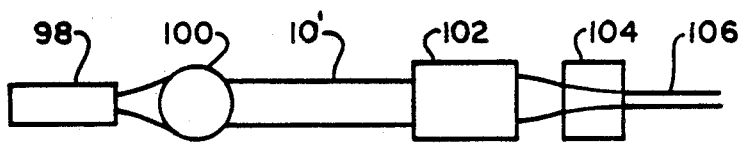
FIG. 1a is a schematic representation of another embodiment of the light source portion that can be employed in a particle size measuring device constructed in accordance with the present invention.
Figure 2:
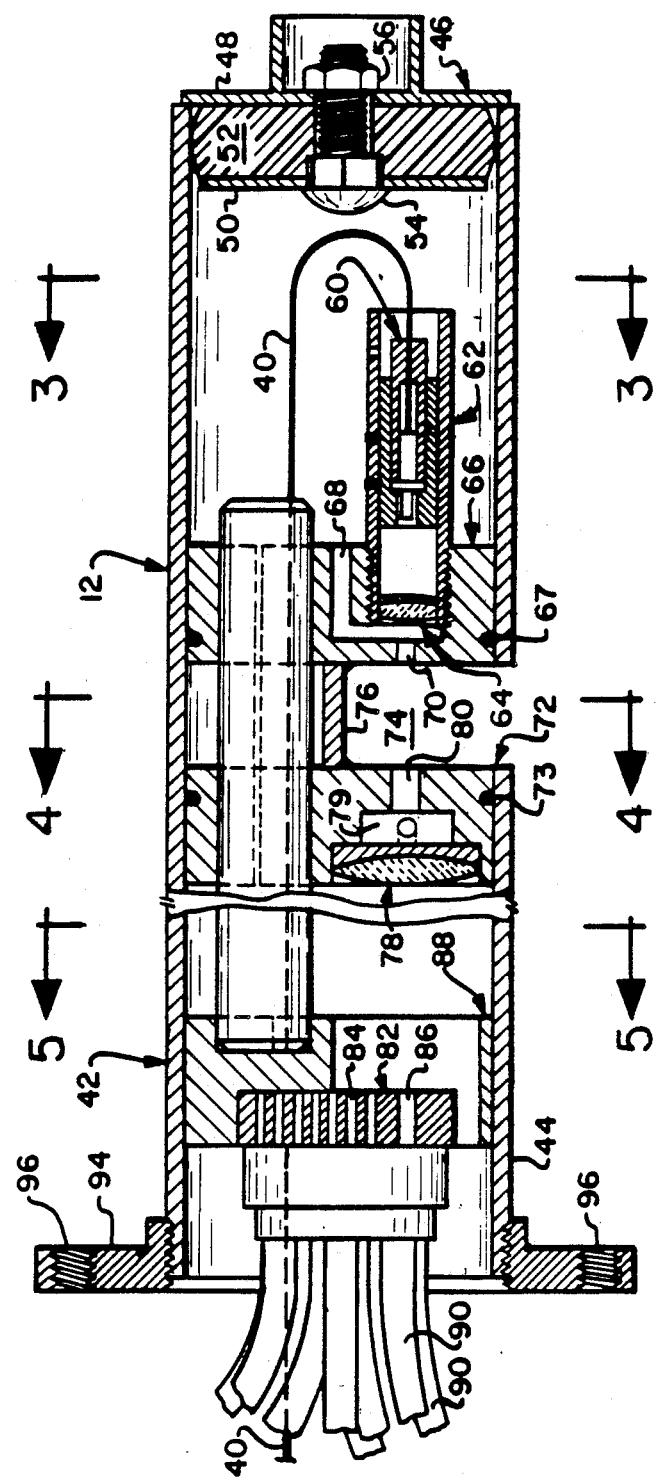
FIG. 2 is a side elevational view partially in section of the probe head portion of a particle size measuring device constructed in accordance with the present invention.

Referring to the drawing, and more particularly to FIGS. 1, 1a and 2 thereof, there is depicted therein a measuring device that is particularly suited for employment for purposes of effecting measurements simultaneously and in situ of the particle size distribution and volumetric density of particles that are present in a fluid substance. In accord with the best mode embodiment of the invention, the subject particle size measuring device consists of two principal components; namely, a light source portion, generally designated by the reference numeral 10 in FIG. 1 of the drawing, and a probe head portion, generally designated by the reference numeral 12 in FIG. 2 of the drawing.

Turning first to a consideration of the nature of the construction of the light source portion 10 of the particle size measuring device constructed in accordance with the present invention, reference will be had for this purpose in particular to FIG. 1 of the drawing. In accordance with the best mode embodiment of the invention, the light source which preferably is utilized in the particle size measuring device of the present invention is a helium neon laser, the latter being generally designated by the reference numeral 14 in FIG. 1. Although for purposes of the description that follows hereinafter of the particle size measuring device of the present invention the light source 14 is described as being a gas laser, i.e., a helium neon laser, it is to be understood that the light source 14 could also take the form of a semiconductor laser without departing from the essence of the present invention. Namely, in spite of the fact that the light source which is required to be employed for purposes of providing the particle size measuring device of the present invention with the mode of operation desired therefrom has been found to necessitate the use of a laser, the specific form of laser that is employed for this purpose may be either that of a gas laser or that of a semiconductor laser. To this end, reference will be had hereinafter to FIG. 1a of the drawing for a description of a light source portion, generally designated therein by the reference numeral 10', which includes a semiconductor laser and which is suitable for use as the light source 14 in a particle size measuring device constructed in accordance with the present invention.

With further reference to FIG. 1 of the drawing, the laser 14 as best understood with reference thereto is designed to be totally housed within an enclosure, the latter being generally designated in FIG. 1 by the reference numeral 16. More specifically, the enclosure 16 in accord with the illustration thereof in FIG. 1 of the drawing consists of a base 18, a pair of end walls 20, a top wall 22, and a pair of side walls 24, only one of which is visible in FIG. 1. As depicted in FIG. 1, the laser 14 is designed to be mounted within the enclosure 16 such that the laser 14 is made to rest on a support block, which can be seen in FIG. 1 at 26. The support block 26 is suitably fastened to the inner surface of the base 18 through the use of any suitable conventional form of fastening means such as threaded fasteners (not shown). For purposes of retaining the laser 14 in supported relation on the support block 26, the laser 14 is preferably clamped to the support block 26 by means of a laser clamp, the latter being designated in FIG. 1 by the reference numeral 28. The clamping action required in order to clamp the laser 14 between the laser clamp 28 and the support block 26 is preferably accomplished through the use of any conventional form of fastening means such as threaded fasteners (not shown) that can be utilized for purposes of effectuating the interengagement of the laser clamp 28 with the support block 26.

The laser 14 obtains its power from a laser power supply, generally designated in FIG. 1 by the reference numeral 30. The laser power supply 30 is suitably mounted within the enclosure 16 on the inner surface of the base 18 thereof through the use of any conventional form of fastening means such as threaded fasteners (not shown). The laser power supply 30 may take the form of any commercially available type of laser power supply that is suitable for use for the aforedescribed purpose of providing power to a helium neon laser. The laser power supply 30 as shown in FIG. 1 is connected to the laser 14 by means of the cable denoted by the reference numeral 32 in FIG. 1, and through which power is provided from the laser power supply 30 to the laser 14. The laser power supply 30 itself in turn is connected by means of the cable seen at 34 in FIG. 1 of the drawing to an external power supply (not shown) from which the power is derived for the laser power supply 30. To this end, the cable 34 exits through an opening (not shown) provided for this purpose in one of the end walls 20 of the enclosure 16 and in doing so is thereafter made to pass through a conduit fitting, the latter being illustrated at 36 in FIG. 1.

Mounted so as to be spaced from but in alignment with the beam of light that the laser 14 generates is a fiberoptic coupler, the latter being denoted generally in FIG. 1 by the reference numeral 38. The fiberoptic coupler 38 is designed to be operative to receive the beam of light from the laser 14 and to cause this beam of light to be coupled to a fiberoptic cable, the latter being denoted by the reference numeral 40 in both FIGS. 1 and 2. The fiberoptic cable 40 in turn is designed to be operative to transmit the beam of light from the laser 14 in the light source portion 10 to the probe head portion 12 of the particle size measuring device of the present invention. To this end, the fiberoptic cable 40 is made to be of sufficient length so as to extend, as best understood with reference to FIGS. 1 and 2 of the drawing from the light source portion 10 to the probe head portion 12. Any conventional form of fiberoptic coupler which is suitable for use as described above and that is available for purchase commercially may be selected for use as the fiberoptic coupler 38 in the particle size measuring device of the present invention. By way of exemplification and not limitation, one such form of commercially available fiberoptic coupler that has been found to be suitable for use as the fiberoptic coupler 38 in the particle size measuring device of the present invention is that marketed by Newport Research under the designation F915.

As had been mentioned herein previously, the light source 14 depicted in FIG. 1 of the drawing could also take the form of a semiconductor laser without departing from the essence of the present invention. To this end, reference is had here to FIG. 1a of the drawing wherein there is to be found depicted the light source portion 10, which utilizes as a light source a laser diode, the latter being denoted therein by the reference numeral 98. It is thus to be understood that the laser diode 98 could equally well serve as the light source 14 for a particle size measuring device constructed in accordance with the present invention in lieu of the helium neon gas laser depicted at 14 in FIG. 1 of the drawings to which reference has been had hereinbefore in connection with the description set forth herein of the nature of the construction of the light source portion 10 illustrated in FIG. 1. With further reference, therefore, to FIG. 1a of the drawings, the laser light emitted from the laser diode 98 is, in accordance with the nature of the construction of the light source portion 10, illustrated in FIG. 1a, received by a spherical lens, the latter being denoted by the reference numeral 100 in FIG. 1a. From the spherical lens 100, the laser light is next transmitted to the graded index lens denoted by the reference numeral 102 in FIG. 1a, and thereafter to the rod lens, which can be found identified in FIG. 1a by the reference numeral 104. After leaving the rod lens 104, the laser light is designed to be transmitted by the single mode fiber, the latter being identified by the reference numeral 106 in FIG. 1a, to the probe head portion 12 of the particle size measuring device of the present invention in a manner similar to that which has been described previously herein in connection with the discussion of the manner in which the light generated by the helium neon gas laser, i.e., light source 14, in FIG. 1 of the drawing is transmitted by the fiberoptic cable 40 from the light source portion 10 to the probe head portion 12 of the particle size measuring device of the present invention.

Continuing with the description of the nature of the construction of the particle size measuring device of the present invention, attention will next be directed to the nature of the construction of the probe head portion 12 thereof. For this purpose, reference will be had in particular to FIG. 2 of the drawing. Thus, the probe head portion, as best understood with reference to FIG. 2, includes an optics enclosure that in FIG. 2 is denoted generally by the reference numeral 42. In accord with the best mode embodiment of the present invention the optics enclosure 42 preferably embodies the form of a tubular member, i.e., a pipe-like member, one end of which as seen at 44 in FIG. 2 is threaded, for a purpose yet to be described. It is through the threaded end of the optics enclosure 42 that the fiberoptic cable 40, to which reference has been had hereinbefore and by means of which the beam of light generated by the laser 14 located in the light source portion 10 of the particle size measuring device of the present invention is transmitted from the light source portion 10 to the probe head portion 12, is made to enter the latter.

The other end of the optics enclosure 42 is designed to be closed. This is accomplished through the utilization of what is commonly referred to in the prior art as a "freeze plug", the latter being denoted generally in FIG. 2 by the reference numeral 46. Inasmuch as the nature of the construction and the mode of operation of freeze plugs such as the freeze plug that bears the designation 46 in FIG. 2 are well-known, it is not deemed necessary for purposes of acquiring an understanding of the present invention that there be set forth herein a detailed description thereof. Suffice it to say that the freeze plug 46 includes a first member identified by the reference numeral 48 in FIG. 2 which is suitably dimensioned so as to embody a diameter that exceeds the internal diameter of the optics enclosure 42 such that when the first member 48 is positioned in abutting engagement with the open end of the optics enclosure 42 in the manner depicted in FIG. 2, the first member 48 is operative to close off the otherwise open end of the optics enclosure 42. The freeze plug 46 further encompasses a second member, the latter being seen at 50 in FIG. 2 of the drawing. In contrast to the first member 48, the second member 50 is suitably dimensioned so as to embody a diameter which is less than the internal diameter of the optics enclosure 42 as measured at the right-hand end thereof as viewed with reference to FIG. 2 such that the second member 50 is capable of being inserted within the optics enclosure 42 in the manner depicted in FIG. 2. Interposed between the first member 48 and the second member 50 is a suitably dimensioned body of compressible material identified in FIG. 2 by the reference numeral 52 which when by virtue of the tightening of the threaded fastener 54 and the nut 56 is caused to become compressed between the first member 48 and the second member 50 a seal is effectuated thereby between the body 52 of compressible material and the inner wall surface of the optics enclosure 42.

Referring further to FIG. 2 of the drawing, it can be seen therefrom that the fiberoptic cable 40 after entering the optics enclosure 42 through the threaded end 44 thereof extends through substantially the entire length of the optics enclosure 42. As best understood with reference to FIG. 2 of the drawing, the fiberoptic cable 40 at the right hand end thereof as viewed with reference to FIG. 2 is cooperatively associated with a fiberoptic coupler, the latter being denoted generally in FIG. 2 by the reference numeral 60. The fiberoptic coupler 60 is designed to be operative for purposes of causing the beam of light being transmitted from the laser 14 through the fiberoptic cable 40 to exit therefrom when this beam of light reaches the end of the fiberoptic cable 40 that is located within the probe head portion 12. As in the case of the fiberoptic coupler 38 to which the other end, i.e., the end of the fiberoptic cable 40 that is located within the light source portion 10, is coupled, any conventional form of fiberoptic coupler which is suitable for use as described above and that is available for purchase commercially may be selected for use as the fiberoptic coupler in the particle size measuring device of the present invention. Further, by way of exemplification and not limitation, one such form of commercially available fiberoptic coupler that has been found to be suitable for use as the fiberoptic coupler 60 in the particle size measuring device of the present invention is that marketed by Seiko Instruments under the designation SF-1A.

After being decoupled from the fiberoptic cable 40 by the fiberoptic coupler 60, the laser beam of light upon exiting from the fiberoptic cable 40 is spatially filtered and collimated. The need for collimation stems from the fact that the laser light beam leaves the fiberoptic cable 40 in the form of a cone. Consequently, as will become more apparent from the discussion that follows hereinafter there is a need to effectuate a change insofar as the light rays are concerned from that of a mode wherein the light rays upon exiting the fiberoptic cable 40 converge to a mode wherein after collimation the light rays are parallel one to another. To this end, positioned in surrounding relation to the fiberoptic coupler 60 is a collimator enclosure, the latter being denoted generally in FIG. 2 by the reference numeral 62. Following collimation, the laser light beam is made to focus on a first focusing means, which is identified generally in FIG. 2 by the reference numeral 64. In accord with the best mode embodiment of the invention, the first focusing means 64 preferably consists of a specially corrected lens which to those skilled in the art is known as an achromatic lens.

It is important for the proper operation of the particle size measuring device of the present invention that the lens 64 be located a predetermined distance from the end of the fiberoptic cable 40 from which the laser beam of light exits. More specifically, in accord with the best mode embodiment of the invention, the lens 64 should be located a distance of one focal length from the end of the fiberoptic cable 40. The lens 64 further is designed to be suitably mounted within a first lens holder/bulkhead means, the latter being designated generally in FIG. 2 by the reference numeral 66. With additional reference to FIG. 2 of the drawing, it can be seen that the collimator enclosure 62 to which reference has been previously had hereinbefore is in turn in accord with the illustrated embodiment of the invention secured in place relative to the first lensholder/bulkhead means 66 by virtue of being threadedly engaged thereto. To this end, both collimator enclosure 62 and the first lensholder/bulkhead means 66 are each provided with a multiplicity of threads that are suitably selected so that they will mate one with another in order to accomplish the aforedescribed threaded engagement therebetween. Finally, it will be apparent with reference to the illustration thereof in FIG. 2 that the first lensholder/bulkhead means 66 is positioned within the optics enclosure 42 so as to be operative to establish a bulkhead within the optics enclosure 42 at a point intermediate the ends thereof. In accord with the nature of the construction of the embodiment of the probe head portion 12 illustrated in FIG. 2 of the drawing, O-rings, one of which can be seen at 67 in FIG. 2, are preferably utilized in order to assist in the establishment of the proper alignment and insertion of the first lensholder/bulkhead means 66 within the optics enclosure 42.

Figure 3:
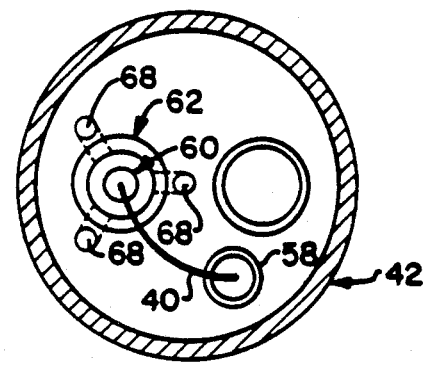
FIG. 3 is a cross-sectional view of the probe head portion of the particle size measuring device constructed in accordance with the present invention of FIG. 2 taken substantially along the line 3—3 in FIG. 2.
Figure 4:
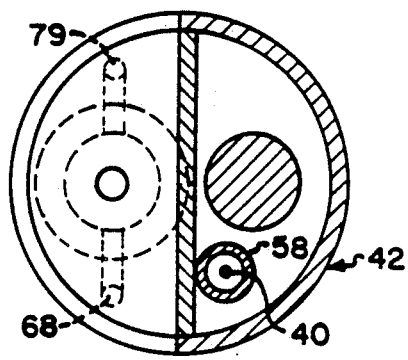
FIG. 4 is a cross-sectional view of the probe head portion of the particle size measuring device constructed in accordance with the present invention of FIG. 2 taken substantially along the line 4—4 in FIG. 2.

It is important for purposes of ensuring the successful operation of the particle size measuring device which comprises the subject matter of the present invention that the lens 64 be kept clean, i.e., that contaminants are not permitted to collect on the front surface thereof, i.e., the left end of the lens 64 as viewed with reference to FIG. 2 of the drawing. In accord with the best mode embodiment of the invention, therefore, purge air is preferably made to flow past the aforereferenced front face of the lens 64. To this end, the first lensholder/bulkhead means 66 has suitably formed therewithin a passage means which has been identified by the reference numeral 68 in FIG. 2 through which the purge air is caused to flow. The passage means 68 in turn is operatively connected in a suitable manner to a purge air supply tube, the latter being seen at 58 in FIGS. 3 and 4 of the drawing, which in turn is designed to be connected in fluid flow relation to a source of supply of purge air suitable for use for the aforedescribed purpose. Although air is preferably employed as the purging fluid in accord with the best mode embodiment of the invention, it is also possible to utilize other types of fluid for this purpose as long as the fluid that is selected for use in this regard possesses the same refractive index as the fluid in which the particles that are to be measured are entrained. Otherwise, if the refractive index of the purging fluid were to be different from the refractive index of the fluid in which the particles to be measured are entrained the accuracy of the measurements of the particles which are obtained through the use of the particle size measuring device of the present invention could be adversely affected.

Referring again to FIG. 2 of the drawing, it can be seen therefrom that in addition to the aforedescribed passage means 68 the first lensholder/bulkhead means 66 also has formed therein an aperture, the latter being seen at 70 in FIG. 2. The aperture 70 is intended to perform a dual function. First, the aperture 70 functions as an outlet for the purging fluid that flows past the face of the lens 64. Secondly, the aperture 70 is suitably aligned with the lens 64 such that the collimated beam of light is focused by the lens 64 in such a manner as to cause the collimated beam of light to pass through the aperture 70 for a purpose yet to be described. Insofar as the dimensions of the aperture 70 are concerned, the latter is sized in relation to the diameter of the laser light beam. More specifically, the aperture 70 is preferably dimensioned so as to be slightly smaller in diameter than the diameter of the laser light beam whereby the outer fringes of the light beam coming from the lens 64 do not pass through the aperture 70, i.e., are eliminated.

Continuing with the description of the nature of the construction of the probe head portion 12 of the particle size measuring device of the present invention, as seen with reference to FIG. 2 of the drawing the probe head portion 12 embodies a second lensholder/bulkhead means, the latter being denoted generally in FIG. 2 by the reference numeral 72. Like the first lensholder/bulkhead means 66 which has been described hereinbefore, the second lensholder/bulkhead means 72 is designed to be emplaced within the optics enclosure 42 whereby a bulkhead is established therewithin by the second lensholder/bulkhead means 72. To this end, in accord with the nature of the construction of the probe head portion 12 illustrated in FIG. 2 of the drawings, O-rings, one of which can be seen at 73 in FIG. 2, are preferably utilized in order to assist in the establishment of the proper alignment and insertion of the second lensholder/bulkhead means 72 within the optics enclosure 42. Any suitable conventional form of fastening means (not shown) may be utilized for purposes of securing the second lensholder/bulkhead means 72 as well as the first lensholder/bulkhead means 66 in place within the optics enclosure 42. As can be seen with reference to FIG. 2 of the drawing when so emplaced within the optics enclosure 42 the second lensholder/bulkhead means 72 is suitably spaced from the first lensholder/bulkhead means 66 so as to be located a predetermined distance therefrom. For purposes of the description set forth herein of the particle size measuring device of the present invention the opening that is formed in the optics enclosure 42, i.e., the space that exists between the first lensholder/bulkhead means 66 and the second lensholder/bulkhead means 72 is referred to as the "sample path", and for ease of identification in connection with the discussion thereof herein is denoted by the reference numeral 74 in FIG. 2. To seal off the sample path 74 from the interior of the optics enclosure 42 a seal plate, seen at 76 in FIG. 2, is preferably secured to both the first lensholder/bulkhead means 66 and the second lensholder/bulkhead means 72 through the use of any suitable conventional form of securing means such as by being welded thereto.

The second lensholder/bulkhead means 72, as the name thereof indicates is designed to be operative to hold a second focusing means, the latter being identified generally in FIG. 2 by the reference numeral 78. In accord with the best mode embodiment of the invention the second focusing means 78 preferably consists of a specially corrected lens which to those skilled in the art is known as an achromatic lens. The achromatic lens 78 for reasons yet to be described is intentionally made to embody dimensions such that the lens 78 in size exceeds the size of the lens 64.

As in the case of the lens 64 to which reference has been had previously herein, it is likewise important from the standpoint of ensuring the successful operation of the particle size measuring device which comprises the subject matter of the present invention that the lens 78 be kept clean, i.e., that contaminants are not permitted to collect on the front surface thereof, i.e., the right end of the lens 78 as viewed with reference to FIG. 2 of the drawing. In accord with the best mode embodiment of the invention, therefore, purge air is preferably made to flow past the aforereferenced front face of the lens 78. To this end, the second lensholder/bulkhead means 72 has suitably formed therewithin a passage means which has been identified by the reference numeral 79 in FIG. 2 through which the purge air is caused to flow. The passage means 79 in turn is operatively connected in fluid flow relation to a source of supply of purge air that is suitable for use for the aforedescribed purpose. Here also it is to be noted that although air is preferably employed as the purging fluid in accord with the best mode embodiment of the invention, it is also possible to utilize other types of fluid for this purpose as long as the fluid that is selected for use in this regard possesses the same refractive index as the fluid in which the particles that are to be measured are entrained. Otherwise, if the refractive index of the purging fluid were to be different from the refractive index of the fluid in which the particles to be measured are entrained the accuracy of the measurements of the particles which are obtained through the use of the particle size measuring device of the present invention could be adversely affected.

With further reference thereto, the second lensholder/bulkhead means 72 in accord with the nature of the construction thereof and as illustrated in FIG. 2 of the drawing has an aperture, the latter being seen at 80 in FIG. 2, formed therein such that the aperture 80 in the second lensholder/bulkhead means 72 is aligned with but located on the opposite of the sample path 74 from the aperture 70 with which as has been described previously hereinbefore the first lensholder/bulkhead means 66 is suitably provided. The aperture 80 is intentionally made to embody dimensions such that the aperture 80 is larger than the aperture 70. Basically, the reason for this is that the light beam upon exiting from the aperture 70 is caused to be focused across the sample path 74. In the course of crossing the sample path 74, the light rays that collectively comprise the light beam, in a manner which will be described more fully hereinafter, are scattered as a result of striking particles that are present in the area of the sample path 74. Thus, the aperture 80 is suitably sized in order to be of sufficient size so as to ensure that the light rays which are scattered by virtue of striking against the particles that are present in the area of the sample path 74 will be captured in the aperture 80 and will be subsequently transmitted therethrough to the second focusing means, i.e., the achromatic lens 78. In summary, in accord with the best mode embodiment of the invention the aperture 80 is made to be larger than the aperture 70. This stems from the need to compensate for the fact that the light rays when they leave the aperture 70 are unscattered whereas when the same light rays reach the aperture 80 at least some of them have been scattered. In this regard, the exact size that the aperture 80 is made is a function of the extent to which the light rays are scattered, which in turn is a function of the size of the particles that by virtue of being struck by the light rays cause the light rays to become scattered, and to a lesser extent the exact size that the aperture 80 is made to embody is a function of the dimensions of the sample path 74. Finally, mention is made here of the fact that the aperture 80 performs the further function of serving as an outlet for the purging fluid that flows past the face of the lens 78.

After crossing the sample path 74 and being received in the aperture 80, the scattered light is then transmitted to the lens 78. The lens 78 is designed to be operative to receive the scattered light and to cause the scattered light to be focused on a detector means, the latter being denoted generally in FIG. 2 by the reference numeral 82, and to which further reference will be had hereinafter. The lens 78, as has been noted previously hereinbefore, is intentionally made to be larger than the lens 64. The reason for this is essentially the same as the reason why the aperture 80 is made to be larger than the aperture 70. Namely, the light rays when they are focused by the lens 64 have not as yet been subjected to scattering whereas when they are received by the lens 78 they have been subjected to a scattering effect in the course of traversing the sample path 74.

Figure 5:
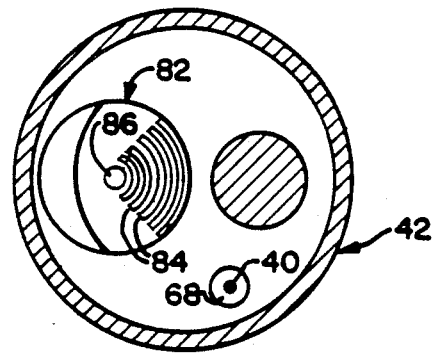
FIG. 5 is a cross-sectional view of the probe head portion of the particle size measuring device constructed in accordance with the present invention of FIG. 2 taken substantially along the line 5—5 in FIG. 2.

As best understood with reference to FIGS. 2 and 5 of the drawing, the detector means 82 in accord with the best mode embodiment of the invention preferably takes the form of a ring-like member. For a purpose yet to be described, the ring-like member 82 is made to embody a multiplicity of arc-like ring segments, each of the latter segments being denoted by the same reference numeral, i.e., 84, in both FIGS. 2 and 5 of the drawing. In addition, at the center thereof the ring-like member 82 has an optical port, seen at 86 in both FIGS. 2 and 5, formed therethrough.

A detector holder/bulkheads means, the latter being identified by the reference numeral 88 in FIG. 2, is utilized in accord with the illustrated embodiment of the invention for purposes of effectuating the proper positioning of the ring-like member 82 within the optics enclosure 42. To this end, like the first lensholder/bulkhead means 66 and the second lensholder/bulkhead means 72 that have been described hereinbefore previously, the detector holder/bulkhead means 88 also performs a dual function. Namely, the detector holder/bulkhead means 88 serves as the means by which the ring-like member 82 is held in place within the optics enclosure 42. In addition, the detector holder/bulkhead means 88 also serves to establish a bulkhead within the optics enclosure 42 at a point that is spaced along the length thereof such that the ring-like member 82 is located in closer proximity to the left hand end as opposed to the right hand end of the optics enclosure 42 as viewed with reference to FIG. 2 of the drawing. The exact location at which the ring-like member 82 is positioned relative to the lens 78 is a function of the focal length of the latter which in turn is a function of the sizes of particles that it is desired to obtain measurements of through the use of the particle size measuring device which is the subject matter of the present invention. Namely, the focal length of the lens 78 which in turn establishes how far the ring-like member 82 is positioned from the lens 78 determines the range of particle sizes with which the ring-like member 82 is operative. Further, the radial spacing that is provided between the various arc-like ring segments, i.e., rings, 84 with which the ring-like member 82 is provided is a function of the sizes of the particles that it is desired to obtain measurements of through the use of the particle size measuring device constructed in accordance with the present invention. In summary, the objective that is sought to be achieved here is to space the ring-like member 82 from the lens 78 a distance which will ensure that the radial spacing that exists between the individual rings 84 of the ring-like member 82 is the correct spacing for the sizes of the particles that it is desired to obtain measurements of with the particle size measuring device of the present invention.

The amount of light energy which is present at each radial ring 84 of the ring-like member 82 is a function of the sizes of the particles that effectuate a scattering of the light rays produced by the laser 14 as these light rays traverse the sample path 74. To this end, the effect of the scattering of the light beam as it traverses the sample path 74 is such that larger size particles produce more light intensity in the rings 84 that are located closer to the center of the ring-like member 82, i.e., closer to the detector center 86 of the ring-like member 82. The converse is also true, i.e., smaller size particles produce more light intensity in the rings 84 that are located furthest from the center of the ring-like member 82, i.e., furthest from the detector center 86 of the ring-like member 82. As a consequence, it is possible to make determinations with respect to particle sizing from the observance of the light intensity that is seen at the various radial rings 84 of the ring-like member 82.

In accord with the best mode embodiment of the invention, such determinations as to particle sizing are accomplished at a location other than within the probe head portion 12 itself of the particle size measuring device of the present invention. To this end, each of the radial rings 84 of the ring-like member 82 as well as optical port, i.e., detector center, 86 have cooperatively associated therewith a plurality of fiberoptic cables, which can be seen illustrated at 90 in FIG. 2 of the drawings. As will be familiar to those who are skilled in this art, each of these fiberoptic cables 90 is designed to function in the manner simply of that of a light conduit. Each group of fiberoptic cables 90 that is associated with a given one of the radial rings 84 as well as optical port, i.e., detector center, 86 of the ring-like member 82 is connected at the other end to a single photodiode, the latter being denoted in FIG. 6 by the reference numeral 92. That is, each ring 84 as well as optical port, i.e., detector center, 86 of the ring-like member 82 is connected through a plurality of fiberoptic cables 90 to a separate photodiode 92. The intent here is to have each of these photodiodes 92 function as an undisturbed focal point for the light that is seen at the particular radial ring 84 as well as optical port, i.e., detector center, 86 of the ring-like member 82 to which the respective photodiode 92 is connected through a given set of fiberoptic cables 90. Each of these photodiodes 92 functions further to produce in known fashion a current that is proportional to the light intensity which is seen at the particular radial ring 84 as well as optical port, i.e., detector center, 86 of the ring-like detector member 82 to which the respective photodiode 92 is connected through a given set of fiberoptic cables 90. This current in turn can be put to various uses to which further reference will be had hereinafter depending upon the nature of the particular application in which it is desired to employ the particle size measuring device which forms the subject matter of the present invention.

Figure 6:
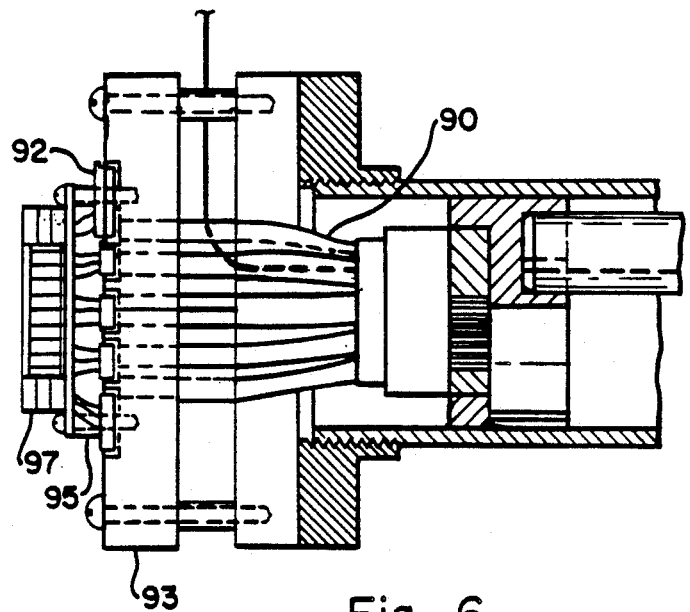
FIG. 6 is a cross-sectional view of a section of the probe head portion of the particle size measuring device constructed in accordance with the present invention depicting the interrelationship that exists between certain of the components of the probe head portion.

With further reference to FIG. 6 of the drawing, in accord with the embodiment of the invention depicted therein, the photodiodes 92 are suitably held in place through the use of a cable/diode holder, the latter being denoted in FIG. 6 by the reference numeral 93. Moreover, in accord with the best mode embodiment of the invention there is cooperatively associated with the photodiodes 92 in turn and as illustrated in FIG. 6 a SA-100 amplifier board, seen at 95 in FIG. 6 and a 20-pin connector, the latter being designated by the reference numeral 97 in FIG. 6. Thus, the signals generated by the photodiodes 92 after being amplified are designed to be fed from the 20-pin connector 97 to any suitable location whereat it is-desired to employ the information relating to particle size that is derived through the use of the particle size measuring device constructed in accordance with the present invention.

There are several specific advantages that are derived as a consequence of utilizing a construction wherein the scattered light rays are focused on a ring-like member such as the ring-like member 82 rather than on photodiodes directly. One of these stems from the fact that a fiberoptic detector consisting of a detector means such as the detector means 82 and to which are connected the fiberoptic cables 90 can be provided at lower cost than the cost to provide the components which would be necessitated if the scattered light rays were to be focused on photodiodes directly. Reference is had here particularly to the cost associated with providing the number of photodiodes that would be required in order to generate the same information concerning the sizes of the particles that occasioned the scattering of the light rays as that which it is possible to generate through the use of the ring-like member 82 and the fiberoptic cables 90. Another one of the benefits that is derived from the use of a fiberoptic detector such as that constructed in the manner of the detector means 82 and fiberoptic cables 90 which can be found illustrated in FIG. 2 of the drawing is that such a fiberoptic detector is operative to establish a barrier between the optics portion and the electrical portion of the particle size measuring device of the present invention. As such, by virtue of the separation of the optics portion from the electrical portion of the particle size measuring device of the present invention, it is possible to utilize the particle size measuring device of the present invention in applications wherein the nature of the fluid medium in which the particles to be measured are entrained would render it hazardous to employ a particle size measuring device wherein the optics portion and the electrical portion thereof were not separated in the manner in which they are in a particle size measuring device constructed in accordance with the present invention.

To complete the description of the nature of the construction of the probe head portion 12 of the particle size measuring device of the present invention, the probe head portion 12 in accord with the embodiment thereof illustrated in FIG. 2 of the drawing at the threaded end 44 of the optics enclosure 42 thereof has cooperatively associated therewith a mounting flange, the latter being denoted by the reference numeral 94 in FIG. 2. As depicted in FIG. 2 the mounting flange 94 is preferably internally threaded so as to be capable of being threadedly engaged with the threaded end 44 of the optics enclosure 42 for purposes of effectuating the securing of the mounting flange 94 to the optics enclosure 42. Continuing, by making use of the mounting flange 94 it is possible to locate the probe head portion 12 of the particle size measuring device of the present invention such that the sample path 74 which the probe head portion 12 embodies is suitably positioned relative to the flow stream of the fluid medium in which the particles are entrained for which measurements relating to the sizes thereof are desired to be obtained through the use of the particle size measuring device of the present invention. To this end, in the case of those applications wherein concern over the wear of the probe head portion 12 occasioned by the presence of the probe head portion 12 in the flow stream of the fluid medium is not a consideration, the probe head portion 12 of the particle size measuring device of the present invention may be permanently emplaced in the flow stream of the fluid medium in which the particles for which measurements are sought to be obtained are entrained. This can be accomplished by securing the mounting flange 94 and thereby the probe head portion 12 to a suitable support (not shown) through the use of any conventional form of securing means (not shown) such as conventional threaded fasteners (not shown) which are received in the openings seen at 96 in FIG. 2 with which the mounting flange 94 is suitably provided for this purpose. For other applications in which concern over the wear of the probe head portion 12 of the particle size measuring device of the present invention is a consideration and/or because the width of the flow stream of the fluid medium in which the particles are entrained is sufficiently large as to render it desirable to take measurements of particles at various locations, i.e., to be able to position the sample path 74 embodied within the optics enclosure 42 of the probe head portion 12 at various points within the flow stream, there may exist a need to employ a mode of operation wherein the probe head portion 12 of the particle size measuring device of the present invention is periodically inserted into the flow stream and then caused to be retracted therefrom. A mechanism that is suitable for use for purposes of accomplishing such insertion and retraction of the probe head portion 12 and thereby the same path 74 within the flow stream of the fluid medium in which the particles are entrained for which measurements are sought to be obtained through the use of the particle size measuring device of the present invention forms the subject matter of the commonly assigned, copending U.S. patent application, Ser. No. 828,479, entitled "Mounting and Traversing Assembly For In Situ Particle Size Measuring Device", which concurrently with the filing of the instant application was filed in the name of Mark P. Eramo and John M. Holmes, which issued as U.S. Pat. No. 4,665,760 on May 19, 1987.

There will now be set forth a description of the mode of operation of the particle size measuring device, which forms the subject matter of the present invention. For this purpose, reference will be had in particular to FIGS. 1 and 2 of the drawing. In accord with the mode of operation of the particle size measuring device of the present invention, light from the helium neon laser 14 is transmitted through a fiberoptic cable 40 from the light source portion 10 of the particle size measuring device constructed in accordance with the present invention to the probe head portion 12 thereof. Within the probe head portion 12, the light exits from the fiberoptic cable 40, is spatially filtered and collimated. The collimated beam of light thereafter is made to traverse the sample path 74. In the course of traversing the sample path 74, the light as a result of striking the particles that are present in the area of the sample path 74 is scattered. This scattered light in turn is gathered by the lens 78 which causes the scattered light to then be focused on the detector means 82. The intensity distribution of the light seen by the detector means 82 is representative of the size of the particles which by virtue of being struck by the light causes the light to be scattered. The detector means 82 is optimized to gather light energy at the radial rings 84 as well as the optical port, i.e., detector center, 86 of the ring-like member 82 which correspond to the critical particle sizes. From the detector means 82 the light is transmitted to a plurality of photodiodes 92, each of which functions to produce a current that is representative of the intensity of the light that has been received by that particular photodiode 92 from which the current emanates. These currents that emanate from the photodiodes 92 can be made use of in a variety of different ways. By way of exemplification and not limitation in this regard, these currents can function in the manner of signals which are caused to be fed to a variety of different devices that in turn are operative to effectuate further processing and/or analysis of the signals received thereby. In this connection, as has been mentioned previously hereinbefore, it is possible to infer particle size distribution of the particles present within the sample path 74 from the light distribution seen by the detector means 82. On the other hand, volumetric density of the particles present in the sample path 74 can be calculated by fitting the observed particle density to the observed light transmission. For this purpose, the observed light transmission is assumed to be in accord with the following equation: $T = e^{-L \int C(\lambda, D) N(D) dD}$, where L=path length, C=extinction cross section, λ=wave length, D=droplet diameter and N=particle size distribution. Moreover, for purposes of the equation set forth above the droplet size distribution is calculated by deconvolution of the intensity distribution using Fraunhofer diffraction theory for large particles and MIE scattering theory for small particles.

One particular application for which the particle size measuring device of the present invention is deemed to be especially suited for employment is that involving the performance of particle size measurements of coal that has been pulverized in a bowl mill. More specifically, the particle size measuring device of the present invention can be cooperatively associated with a bowl mill of the type that is designed to be employed for purposes of effectuating the pulverization of coal so as to enable control to be exercised over the operation of the bowl mill based on particle size measurements obtained through the use of the particle size measuring device of the present invention. The manner in which such control is exercised over the operation of a bowl mill using a particle size measuring device constructed in accordance with the present invention forms the subject matter of the commonly assigned, copending U.S. patent application, Ser. No. 828,490, entitled "Pulverized Solid Control System", which concurrently with the filing of the instant application was filed in the names of George F. Shulof and Michael J. DiMonte.

Thus, in accordance with the present invention there has been provided a new and improved measuring device that is operative for purposes of obtaining measurements of the size of particles that are present in a fluid substance. Moreover, the particle size measuring device of the present invention renders it possible through the use thereof to rapidly obtain accurate measurements of particle size. In addition, in accord with the present invention a particle size measuring device is provided through the use of which it is possible to make in situ measurements of the size of particles that are present in a fluid substance. Further, the particle size measuring device of the present invention is operative to effect the measurements in situ of the particle size distribution of particles which are present in a fluid substance. Additionally, in accordance with the present invention the particle size measuring device is operative to effect the measurement in situ of the volumetric density of particles that are present in a fluid substance concurrent with the making of measurements in situ of the particle size distribution of the particles which are present in the fluid substance. Also, the particle size measuring device of the present invention renders it possible through the use thereof to generate information relating to particle size in a sufficiently timely fashion whereby control may be exercised over an industrial process based on the information derived from the particle size measurements. Furthermore, in accordance with the present invention a particle size measuring device has been provided which is relatively simple to manufacture and operate, while yet being relatively inexpensive to provide.

While only one embodiment of our invention has been shown and described herein, it will be appreciated that modifications thereof, some of which have been alluded to hereinabove, may still be readily made thereto by those skilled in the art. We, therefore, intend by the appended claims to cover the modifications alluded to herein as well as all other modifications which fall within the true spirit and scope of our invention.

What is claimed is:

1. A particle size measuring device for obtaining measurements in situ of the size of particles present in a fluid substance having a specific refractive index comprising:

(a.) a probe head portion including a first lensholder mounted therewithin at a first location and a second lensholder mounted therewithin in spaced relation to said first lensholder at a second location, said first lensholder and said second lensholder defining therebetween an open area in said probe head portion operative as a sample path, said first lensholder having an aperture formed therein, said second lensholder having an aperture formed therein, said aperture is said second lensholder being aligned with and being larger in size than said aperture in said first lensholder;

(b.) means for locating said probe head portion within the fluid substance with said probe head portion positioned such that the fluid substance containing the particles to be measured passes through said sample path of said probe head portion;

(c.) a helium neon laser operative for producing a beam of light consisting of a multiplicity of individual light rays;

(d.) first light conveying means comprising a fiberoptic cable, said fiberoptic cable being optically coupled to said helium neon laser so as to be operative to convey the bead of light from said helium neon laser;

(e.) a first achromatic lens having a first face and a second face, said first achromatic lens being mounted in said first lensholder so that said first face thereof is positioned in juxtaposed relation to said aperture in said first lensholder, said first achromatic lens being optically coupled to said fiberoptic cable for receiving the beam of light therefrom said first achromatic lens being operative to focus the beam of light through said aperture formed in said first lensholder and across said sample path such that the particles contained in the fluid substance present in said sample path are operative to cause a scattering of the individual light rays of the beam of light as the beam of light crosses said sample path;

(f.) first purging means including a first passage means formed in said first lensholder so as to be connected in fluid flow relation with said first achromatic lens, said first purging means further including a first purging fluid supply tube supported in said probe portion so as to have one end thereof connected in fluid flow relation with said first passage means, said first purging fluid supply tube being operative to supply to said first passage means a first flow of purging fluid having a refractive index substantially the same as the refractive index of the fluid substance present in said sample path, said first passage means being operative to cause said first flow of purging fluid supplied thereto to flow past said first face of said first achromatic lens for purposes of keeping said first face of said first achromatic lens free of contaminants whereupon said first flow of purging fluid is made to exit through said aperture in said first lensholder;

(g.) a second achromatic lens having a first face and a second face and being larger in size than said first achromatic lens, said second achromatic lens being mounted in said second lensholder so that said first face thereof is positioned in juxtaposed relation to said aperture in said second lensholder, said second achromatic lens being operative to capture those light rays scattered in the course of the passage thereof across said sample path that are received by said aperture formed in said second lensholder;

(h.) second purging means including a second passage means formed in said second lensholder so as to be connected in fluid flow relation with said second achromatic lens, said second purging means further including a second purging fluid supply tube supported in said probe head portion so as to have one end thereof connected in fluid flow relation with said second passage means, said second purging fluid supply tube being operative to supply to said second passage means a second flow of purging fluid having a refractive index substantially the same as the refractive index of the fluid substance present in said sample path, said second passage means being operative to cause said second flow of purging fluid supplied thereto to flow past said first face of said second achromatic lens for purposes of keeping said first face of said second achromatic lens free of contaminants wherein said second flow of purging fluid is made to exit through said aperture in said second lensholder; and (i.) detector means including a ring-like member having a multiplicity of radial rings formed therein, said multiplicity of radial rings being optically coupled to said second achromatic lens for receiving therefrom the light rays scattered in the course of the passage thereof across said sample path captured by said second achromatic lens, said detector means further including a plurality of photodiodes and second light conveying means, said second light conveying means comprising a plurality of groups of fiberoptic cables, said plurality of groups of fiberoptic cables being operative to optically couple said multiplicity of radial rings to said plurality of photodiodes, said plurality of photodiodes being operative based on the intensity of the light of the scattered light rays received by said multiplicity of radial rings and transmitted by means of said plurality of groups of fiberoptic cables to said plurality of photodiodes to generate signals relating to the size of the particles that cause the light rays to be scattered while crossing said sample path.

2. A particle size measuring device for obtaining measurements in situ of the size of particles present in a fluid substance having a specific refractive index comprising:

(a.) a probe head portion including a first lensholder mounted therewithin at a first location and a second lensholder mounted therewithin in spaced relation to said first lensholder at a second location, said first lensholder and said second lensholder defining therebetween an open area in said probe head portion operative as a sample path, said first lensholder having an aperture formed therein, said second lensholder having an aperture formed therein, said aperture in said second lensholder being aligned with and being larger in size than said aperture in said first lensholder;

(b.) means for locating said probe head portion within the fluid substance with said probe head portion positioned such that the fluid substance containing the particles to be measured passes through said sample path of said probe head portion;

(c.) a semiconductor laser operative for producing a beam of light consisting of a multiplicity of individual light rays;

(d.) first light conveying means comprising a fiberoptic cable, said fiberoptic cable being optically coupled to said semiconductor laser so as to be operative to convey the beam of light from said semiconductor laser;

(e.) a first achromatic lens having a first face and a second face, said first achromatic lens being mounted in said first lensholder so that said first face thereof is positioned in juxtaposed relation to said aperture in said first lensholder, said first achromatic lens being optically coupled to said fiberoptic cable for receiving the beam of light therefrom, said first achromatic lens being operative to focus the beam of light through said aperture formed in said first lensholder and across said sample path such that the particles contained in the fluid substance present in said sample path are operative to cause a scattering of the individual light rays of the beam of light as the beam of light crosses said sample path;

(f.) first purging means including a first passage means formed in said first lensholder so as to be connected in fluid flow relation with said first achromatic lens, said first purging means further including a first purging fluid supply tube supported in said probe portion so as to have one end thereof connected in fluid flow relation with said first passage means, said first purging fluid supply tube being operative to supply to said first passage means a first flow of purging fluid having a refractive index substantially the same as the refractive index of the fluid substance present in said sample path, said first passage means being operative to cause said first flow of purging fluid supplied thereto to flow past said first face of said first achromatic lens for purposes of keeping said first face of said first achromatic lens free of contaminants whereupon said first flow of purging fluid is made to exit through said aperture in said first lensholder;

(g.) a second achromatic lens having a first face and a second face and being larger in size than said first achromatic lens, said second achromatic lens being mounted in said second lensholder so that said first face thereof is positioned in juxtaposed relation to said aperture in said second lensholder, said second achromatic lens being operative to capture those light rays scattered in the course of the passage thereof across said sample path that are received by said aperture formed in said second lensholder;

(h.) second purging means including a second passage means formed in said second lensholder so as to be connected to fluid flow relation with said second achromatic lens, said second purging means further including a second purging fluid supply tube supported in said probe head portion so as to have one end thereof connected in fluid flow relation with said second passage means, said second purging fluid supply tube being operative to supply to said second passage means a second flow of purging fluid having a refractive index substantially the same as the refractive index of the fluid substance present in said sample path, said second passage means being operative to cause said second flow of purging fluid supplied thereto to flow past said first face of said second achromatic lens for purposes of keeping said first face of said second achromatic lens free of contaminants whereupon said second flow of purging fluid is made to exit through said aperture in said second lensholder; and (i.) detector means including a ring-like member having a multiplicity of radial rings formed therein, said multiplicity of radial rings being optically coupled to said second achromatic lens for receiving therefrom the light rays scattered in the course of the passage thereof across said sample path captured by said second achromatic lens, said detector means further including a plurality of photodiodes and second light conveying means, said second light conveying means comprising a plurality of groups of fiberoptic cables, said plurality of groups of fiberoptic cables being operative to optically couple said multiplicity of radial rings to said plurality of photodiodes, said plurality of photodiodes being operative based on the intensity of the light of the scattered light rays received by said multiplicity of radial rings and transmitted by means of said plurality of groups of fiberoptic cables to said plurality of photodiodes to generate signals relating to the size of the particles that cause the light rays to be scattered while crossing said sample path.

* * * * *